(12) United States Patent
Salaita et al.

(10) Patent No.: US 11,884,967 B2
(45) Date of Patent: Jan. 30, 2024

(54) POLYNUCLEOTIDE BASED MOVEMENT, KITS AND METHODS RELATED THERETO

(71) Applicant: Emory University, Atlanta, GA (US)

(72) Inventors: Khalid Salaita, Atlanta, GA (US); Kevin Yehl, Atlanta, GA (US)

(73) Assignee: Emory University, Atlanta, GA (US)

( * ) Notice: Subject to any disclaimer, the term of this patent is extended or adjusted under 35 U.S.C. 154(b) by 876 days.

(21) Appl. No.: 16/922,449

(22) Filed: Jul. 7, 2020

(65) Prior Publication Data

US 2020/0332350 A1 Oct. 22, 2020

Related U.S. Application Data

(62) Division of application No. 15/332,007, filed on Oct. 24, 2016, now Pat. No. 10,738,349.

(60) Provisional application No. 62/245,618, filed on Oct. 23, 2015.

(51) Int. Cl.
*C12Q 1/6827* (2018.01)
*C12N 9/22* (2006.01)
*C12Q 1/6825* (2018.01)

(52) U.S. Cl.
CPC .............. *C12Q 1/6827* (2013.01); *C12N 9/22* (2013.01); *C12Q 1/6825* (2013.01); *C12Y 301/26004* (2013.01)

(58) Field of Classification Search
CPC ................ C12Q 1/6827; C12Q 1/6825; C12Q 2521/327; C12Q 2525/121; C12Q 2563/149; C12Q 2565/107; C12Q 2565/131; C12N 9/22; C12Y 301/26004
See application file for complete search history.

(56) References Cited

U.S. PATENT DOCUMENTS

| 5,403,711 | A | 4/1995 | Walder |
| 7,351,557 | B2 | 4/2008 | Kurn |
| 10,738,349 | B2* | 8/2020 | Salaita ................ C12Q 1/6825 |
| 2005/0176029 | A1 | 8/2005 | Heller |
| 2007/0238096 | A1 | 10/2007 | Reich |
| 2011/0281740 | A1 | 11/2011 | Beechem |
| 2012/0263648 | A1 | 10/2012 | Shapiro |

FOREIGN PATENT DOCUMENTS

WO 2015177666 11/2015

OTHER PUBLICATIONS

Bath et al. A Free-Running DNA Motor Powered by a Nicking Enzyme, Angew. Chem. 2005, 117, 4432-4435.
Bishop et al. An Improved Autonomous DNA Nanomotor, Nano Letters, 2007, 7(9),2574-2577 and supplemental materials.
Cha et al. A synthetic DNA motor that transports nanoparticles along carbon nanotubes, Nature Nanotechnology, vol. 9, 2014, 39-43.
Chen et al. An Autonomous DNA Nanomotor Powered by a DNA Enzyme, Angew. Chem. Int. Ed. 2004, 43, 3554-3557.
Gautham, New DNA Molecular Motor Transports Nanoparticles, Labcritics, 2013.
Goodrich et al. Direct Detection of Genomic DNA by Enzymatically Amplified SPR Imaging Measurements of RNA Microarrays, J. Am. Chem. Soc. 2004, 126, 4086-4087.
Gu et al. A Proximity-Based Programmable DNA Nanoscale Assembly Line, Nature. 2010, 465(7295): 202-205.
Halford, Rethinking Molecular Machines—Makers of artificial molecular-scale devices grapple with how to make the field achieve its promise, Chemical and Engineering News, 2012, 90 (41):26-27.
Long et al. Molecular Dynamics Studies of Ion Distributions for DNA Duplexes and DNA Clusters: Salt Effects and Connection to DNA Melting, J. Phys. Chem. B 2006, 110, 2918-2926.
Lund et al. Molecular robots guided by prescriptive landscapes, Nature, vol. 465, 2010, 206-210.
Omabegho et al. A Bipedal DNA Brownian Motor with Coordinated Legs,Science. 2009, 324(5923): 67-71.
Roche, Ribonuclease H (RNase H), From *Escherichia coli* H 560 pol A1, Cat. No. 10 786 357 001.
Yehl et al. High-speed DNA-based rolling motors powered by RNase H, Nat Nanotechnol 2016, 11(2):184-90.
Yin et al. Programming biomolecular self-assembly pathways, Nature Letters, vol. 451, 2008, 318-323.

* cited by examiner

*Primary Examiner* — Narayan K Bhat
(74) *Attorney, Agent, or Firm* — Emory Patent Group

(57) ABSTRACT

This disclosure relates DNA based movement of objects. In certain embodiments, particles, pairs of particles, or rods are conjugated with single stranded DNA that hybridizes to a single stranded RNA that is conjugated to a substrate. When the DNA particle, pair of particles, or rod interacts with the surface RNA in the presence of an endonuclease, such as RNase H and the DNA hybridizes to the RNA, then the particle, pair of particles, or rod moves along the surface. The complementarity of the DNA and RNA affect the velocity.

19 Claims, 13 Drawing Sheets

Specification includes a Sequence Listing.

| ID | Sequence (5'-3') |
|---|---|
| DNA Anchor | /5AmMC6/GAGAGAGATGGGTGCTTTTTTTTTTTTTTTT/3ThiolMC3-D/ (SEQ ID NO: 1) |
| RNA/DNA Chimera Substrate | GCACCCATCTCTCTCrCrCrCrCrCrCrUrGrUrGrArUrUrGrArUrUrArCrU (SEQ ID NO: 2) /3Cy3Sp/ |
| DNA Control Substrate | GCACCCATCTCTCTCCCCCCCTGTGATTGATTACT (SEQ ID NO: 3)/3Cy3Sp/ |
| Particle DNA | /5Hexynyl/TTTTTTTTTTTTTTTAGTAATCAATCACAG (SEQ ID NO: 4) |
| RNA Complement | TTTTTTTTTTTTTTTAGTAATCAATCACAG (SEQ ID NO: 4) |
| Particle Blocking Strand | CTGTGATTGATTACT (SEQ ID NO: 5) |
| Perfect Match | /5Hexynyl/TTTTTTTTTTTTTTTmAmGTAATCAAmUmCACAG (SEQ ID NO: 6) |
| SNP | /5Hexynyl/TTTTTTTTTTTTTTTmAmGTAATTAAmUmCACAG (SEQ ID NO: 7) |

FIG. 1B

5'-AGTAATCAATCACAG-3'   5'-AGTAATTAATCACAG-3'

SEQ ID NO: 6           SEQ ID NO: 7

SEQUENCE LISTING

<160> NUMBER OF SEQ ID NOS: 7

<210> SEQ ID NO 1
<211> LENGTH: 30
<212> TYPE: DNA

-continued

<213> ORGANISM: Artificial
<220> FEATURE:
<223> OTHER INFORMATION: Synthetic

<400> SEQUENCE: 1
gagagagatg ggtgctttt tttttttttt                                30

<210> SEQ ID NO 2
<211> LENGTH: 35
<212> TYPE: DNA
<213> ORGANISM: Artificial
<220> FEATURE:
<223> OTHER INFORMATION: Synthetic

<400> SEQUENCE: 2
gcacccatct ctctcccccc cugugauuga uuacu                          35

<210> SEQ ID NO 3
<211> LENGTH: 35
<212> TYPE: DNA
<213> ORGANISM: Artificial
<220> FEATURE:
<223> OTHER INFORMATION: Synthetic

<400> SEQUENCE: 3
gcacccatct ctctcccccc ctgtgattga ttact                          35

<210> SEQ ID NO 4
<211> LENGTH: 31
<212> TYPE: DNA
<213> ORGANISM: Artificial
<220> FEATURE:
<223> OTHER INFORMATION: Synthetic

<400> SEQUENCE: 4
tttttttttt tttttagta atcaatcaca g                               31

<210> SEQ ID NO 5
<211> LENGTH: 15
<212> TYPE: DNA
<213> ORGANISM: Artificial
<220> FEATURE:
<223> OTHER INFORMATION: Synthetic

<400> SEQUENCE: 5
ctgtgattga ttact                                                15

<210> SEQ ID NO 6
<211> LENGTH: 15
<212> TYPE: DNA
<213> ORGANISM: Artificial
<220> FEATURE:
<223> OTHER INFORMATION: Synthetic

<400> SEQUENCE: 6
agtaatcaau cacag                                                15

<210> SEQ ID NO 7
<211> LENGTH: 15
<212> TYPE: DNA
<213> ORGANISM: Artificial
<220> FEATURE:
<223> OTHER INFORMATION: Synthetic

```
<400> SEQUENCE: 7
agtaattaau cacag                                                    15
```

POLYNUCLEOTIDE BASED MOVEMENT, KITS AND METHODS RELATED THERETO

CROSS REFERENCE TO RELATED APPLICATIONS

This application is a division of U.S. application Ser. No. 15/332,007 filed Oct. 24, 2016, which claims the benefit of U.S. Provisional Application No. 62/245,618 filed Oct. 23, 2015. The entirety of each of these applications is hereby incorporated by reference for all purposes.

STATEMENT REGARDING FEDERALLY FUNDED RESEARCH

This invention was made with government support under R01-GM097399 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 15080USDIV_ST25.txt. The text file is 2 KB, was created on Jun. 30, 2020, and is being submitted electronically via EFS-Web.

BACKGROUND

Converting chemical energy into controlled motion is useful in applications such as sensors, drug delivery platforms, and computing. Bath et al. report a linear motor built from DNA and a restriction enzyme, which moves a DNA cargo in discrete steps along a DNA track. Angew Chem Int Edit 44, 4358-4361 (2005). DNA-based machines that walk along a track have shown promise in recapitulating the properties of biological motor proteins. See Yin et al. Programming biomolecular self-assembly pathways. Nature, 2008, 451, 318-U314; Cha et al., Nat Nanotechnol, 2014, 9, 39-43; Omabegho et al., Science, 2009, 324, 67-71; Gu et al., Nature, 2010, 465, 202-205; and Lund et al., Nature, 2010, 465, 206-210. However, the maximum distance traveled by the most DNA-based motors is 1 μm. The velocity of these walkers is also limited due to a fundamental trade-off between motor endurance and speed. Thus, there is a need to identify improved architectures.

SUMMARY

This disclosure relates DNA based movement of objects. In certain embodiments, particles, pairs of particles, or rods are conjugated with single stranded DNA that hybridizes to a single stranded RNA that is conjugated to a substrate. When the DNA particle, pair of particles, or rod interacts with the surface RNA in the presence of an endonuclease, such as RNase H and the DNA hybridizes to the RNA, then the particle, pair of particles, or rod moves along the surface. The complementarity of the DNA and RNA affect the velocity. In certain embodiments, this disclosure contemplates amplifying a sample nucleic acid into single stranded DNA and conjugating it to the particle, pair of particles, or a rod. Exposing the particle to complementary surface RNA and measuring the velocity which implicates the nucleic acid sequence in the sample.

In certain embodiments, this disclosure relates to devices comprising, a particle, pair of particles or rod comprising a coating of single stranded DNA; a substrate comprising a coating of single stranded RNA; and an endoribonuclease such as RNase H, wherein the single stranded DNA hybridizes to the RNA on the substrate and the particle, pair of particles or rod is configured on the substrate such that the particle, pair of particles, or rod moves upon mixing the endoribonuclease with the DNA hybridized to the RNA.

In certain embodiment, the substrate comprises channels configure to be slightly greater than the diameter of the particle such that the particle, length of a pair of particles, or length of the rod. In certain embodiments, the channels are separated by a barrier of polyethylene glycol. In certain embodiment, the channels are configured such that the object is capable of moving in the channel but is restricted from isolating itself from RNA on the substrate surface.

In certain embodiments, the DNA is between 5 and 500, or 5 and 50, or 5 and 25, or 10 and 50, or 10 and 25 nucleotides in length. In certain embodiments, the particle comprises silica or a semiconductor material, metal or oxide having a polymer coating.

In certain embodiments, the DNA oligonucleotide is 3' or 5' conjugated to the surface of the particle. In certain embodiments, the particle, pair of particles, or rod has a diameter or length of 0.001 micrometers to 1 centimeters, or 0.001 micrometers to 0.1 centimeters, or 0.001 micrometers to 0.01 centimeters, or 0.001 micrometers to 1 micrometer. In certain embodiments, the DNA or the RNA encodes a polynucleotide sequence associates with a polymorphism, SNP, or mutation associated with a genetic disorder. In certain embodiments, the DNA or RNA can encode aptamer or split aptamer sequences associated with binding to aptamer ligand. In certain embodiments, DNA or RNA sequences encodes a catalytic oligonucleotide associated with specific metal cofactors. In certain embodiments, the substrate is a metal surface, glass, polymer, or microscope slide. In certain embodiments, the RNA is conjugated to a fluorescent molecule. In certain embodiments, movement of the particle, pair of particles, or rods are measured for velocity, e.g., random movement or in a single direction.

In certain embodiments, the disclosure relates to methods for moving a particle, pair or particles, or rod comprising DNA, comprising: providing a device comprising, a particle, pair of particles, or rod comprising a coating of single stranded DNA; a substrate comprising a coating of single stranded RNA; and an endoribonuclease such as RNase H, wherein the single stranded DNA hybridizes to the RNA on the substrate and the particle, pair of particles, or rod is configured on the substrate such that the particle, pair of particles, or rod moves upon mixing the endoribonuclease with the DNA hybridized to the RNA; placing the single stranded DNA coated particle, pair or particles, or rod on the surface of the single stranded RNA coated substrate in the presence of the endonuclease under conditions such that the particle, pair of particles, or rod moves on the surface of the substrate.

In certain embodiments, DNA or RNA is a sequence obtained from a sample. In certain embodiments, the speed of the movement of the particle, pair of particles, or rod is correlated to the sequence of the DNA or RNA. In certain embodiments, a maximum speed is associated with complete complementarity. In certain embodiments, a speed of less than the maximum speed is associated with incomplete complementarity.

In certain embodiments, the disclosure relates to kits comprising: a) a pair or primers wherein the primers are configured for amplification of a target DNA sequence, b) a substrate that contains single stranded DNA bound to the surface, and c) an oligonucleotide conjugated to a fluorescent marker wherein the oligonucleotide has a first segment that is complementary to the DNA bonded to the surface of the substrate and a second segment that is RNA and complementary to the target DNA sequence that is to be obtained from a sample by amplification from the pair of primers.

In certain embodiments, the kit further comprises RNase H.

BRIEF DESCRIPTION OF THE DRAWINGS

FIG. 1B shows a figure with oligonucleotide sequences conjugated to dyes and other molecules for support on solid surfaces.

DETAILED DISCUSSION

Figure 1A:
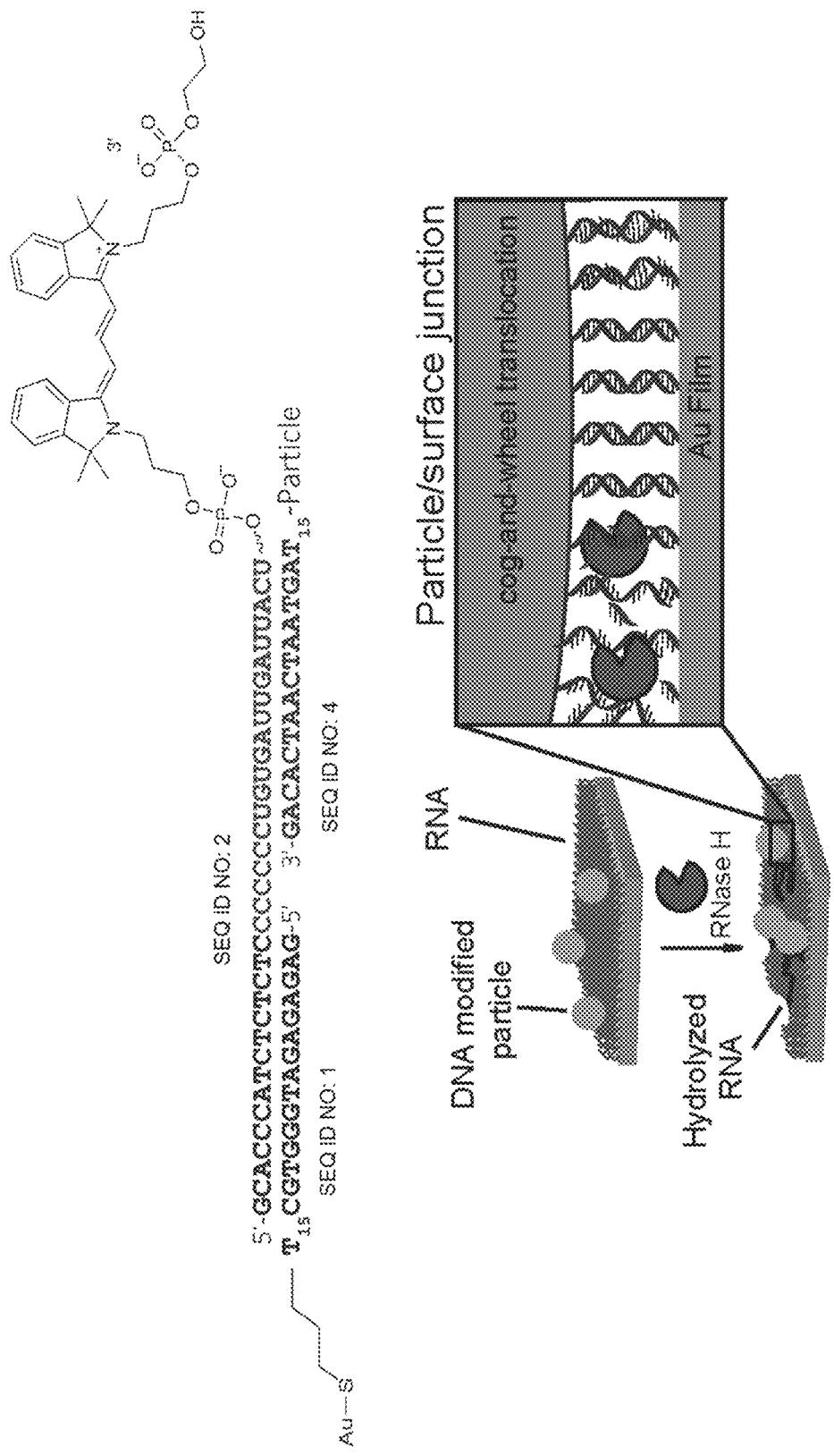
FIG. 1A illustrates an approach for generating RNA-fueled, enzyme catalyzed autonomous DNA motors. DNA-modified particles were hybridized to an RNA monolayer presenting a complementary strand. Particles were immobile until RNase H was added, which selectively hydrolyses RNA duplexed to DNA. Schematic representation showing the hybridized oligonucleotide sequences at the particle-substrate junction. Note that there are hundreds of duplexes within this junction.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA.

As used herein, biological samples include all clinical samples useful for detection of disease in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes blood obtained from a human subject, such as whole blood or serum. In another particular example, a sample includes buccal cells, for example collected using a swab or by an oral rinse.

Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

A mutation refers to a change of a nucleic acid sequence as a source of genetic variation. For example, mutations can occur within a gene or chromosome, including specific changes in non-coding regions of a chromosome, for instance changes in or near regulatory regions of genes. Types of mutations include, but are not limited to, base substitution point mutations (which are either transitions or transversions), deletions, and insertions. Missense mutations are those that introduce a different amino acid into the sequence of the encoded protein; nonsense mutations are those that introduce a new stop codon; and silent mutations are those that introduce the same amino acid often with a base change in the third position of the codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

Polymorphism refers to a variation in a gene sequence. The polymorphisms can be those variations (DNA sequence differences) which are generally found between individuals or different ethnic groups and geographic locations which, while having a different sequence, produce functionally equivalent gene products. Typically, the term can also refer to variants in the sequence which can lead to gene products that are not functionally equivalent. Polymorphisms also encompass variations which can be classified as alleles and/or mutations which can produce gene products which may have an altered function. Polymorphisms also encompass variations which can be classified as alleles and/or mutations which either produce no gene product or an inactive gene product or an active gene product produced at an abnormal rate or in an inappropriate tissue or in response to an inappropriate stimulus. Alleles are the alternate forms that occur at the polymorphism.

A "single nucleotide polymorphism (SNP)" is a single base (nucleotide) polymorphism in a DNA sequence among individuals in a population. Typically, in the literature, a single nucleotide polymorphism (SNP) may fall within coding sequences of genes, non-coding regions of genes, or in the intergenic regions between genes. SNPs within a coding sequence will not necessarily change the amino acid sequence of the protein that is produced, due to degeneracy of the genetic code. A SNP in which both forms lead to the same polypeptide sequence is termed "synonymous" (sometimes called a silent mutation)—if a different polypeptide sequence is produced they are "nonsynonymous". A nonsynonymous change may either be missense or "nonsense", where a missense change results in a different amino acid, while a nonsense change results in a premature stop codon.

Hybridization refers to the ability of complementary single-stranded DNA or RNA to form a duplex molecule (also referred to as a hybridization complex). Nucleic acid hybridization techniques can be used to form hybridization complexes between a probe or primer and a nucleic acid. Hybridizable and hybridizes are terms which indicate a sufficient degree of complementarity such that stable and specific binding occurs between an oligonucleotide and its DNA or RNA target. An oligonucleotide need not be 100% complementary to its target DNA or RNA sequence to be specifically hybridizable. An oligonucleotide is specifically hybridizable when there is a sufficient degree of complementarity to avoid non-specific binding of the oligonucleotide to non-target sequences under conditions in which specific binding is desired. Hybridization conditions resulting in particular degrees of stringency will vary depending upon the nature of the hybridization method and the composition and length of the hybridizing nucleic acid sequences.

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art. The primers disclosed herein can hybridize to nucleic acid molecules under low stringency, high stringency, and very high stringency conditions.

As used herein, Ribonuclease H (RNase H) is a family of non-sequence-specific endonucleases that catalyze the cleavage of RNA via a hydrolytic mechanism. Ribonuclease activity for RNase H cleaves the 3'-O—P bond of RNA in a DNA/RNA duplex substrate to produce 3'-hydroxyl and 5'-phosphate terminated products and the RNase H specifically degrades only the RNA in RNA:DNA complex.

As used herein, conjugated refers to either covalently attaching two or objects together, or creating hydrogen bonding interactions, such as hybridization of two nucleic acids, such that the two objects do not substantially dissociate in a solution of water at room temperature and neutral pH.

In certain embodiments, this disclosure relates to devices comprising, a particle, pair of particles, or rod comprising a coating of single stranded DNA; a substrate comprising a coating of single stranded RNA; and an endoribonuclease such as RNase H, wherein the single stranded DNA hybridizes to the RNA on the substrate and the particle, pair of particles, or rod is configured on the substrate such that the particle, pair of particles or rod, moves upon mixing the endoribonuclease with the DNA hybridized to the RNA.

In certain embodiments, the particle is a conglomerate of matter that is preferably spherical in shape. However, it is contemplated that the particle may not be perfectly spherical, e.g. oval or having imperfections. The diameter of a particle refers to the average size of the diameter. Typically, the size of the particle is such that the location of the particle can be readily identified by visual or other spectroscopic means on a substrate. The particle may be made of a core material that has covalent bonds, e.g., polymers or resins, or from semiconductor materials, e.g., CdSe, CdS, CdTe quantum dots, metals or oxides thereof, e.g., iron oxide particles.

In certain embodiments, a "rod" refers two or more particles that are joined together to form a length that is two or more times the smallest diameter of one of the particles. The rod may be straight or have a slight bend, for example when three or more particles are joined but do not exist in an absolute straight line. In certain embodiments, a rod may be nanotube or other structure that can be conjugated with DNA.

In the case of quantum dot, metal particle or rod, the outer surface may have a polymer coating that is chemically crosslinked to prevent the polymers from separating from the particle or rod.

In certain embodiments, the "coating of single stranded DNA" refers to the conjugation of a nucleic acid to the outer surface of a particle, pair of particles, or rod wherein at least a portion of the DNA sequence is single stranded. The DNA may be hybridizing to a complementary strand that is used to conjugate the DNA to the particle providing a portion of the DNA that is double stranded.

In certain embodiments, a "substrate" refers to a surface that is stationary with respect to the RNA conjugated thereto. Conjugation of single stranded RNA to the substrate may be by hybridization or by covalently linking the RNA. The surface may be planar or curved so long as the surface area is sufficiently large in relation to any particles or rods placed thereon such that movement of the particles or rods from different locations on the surface can be detected.

Methods of Use

Figure 1C:
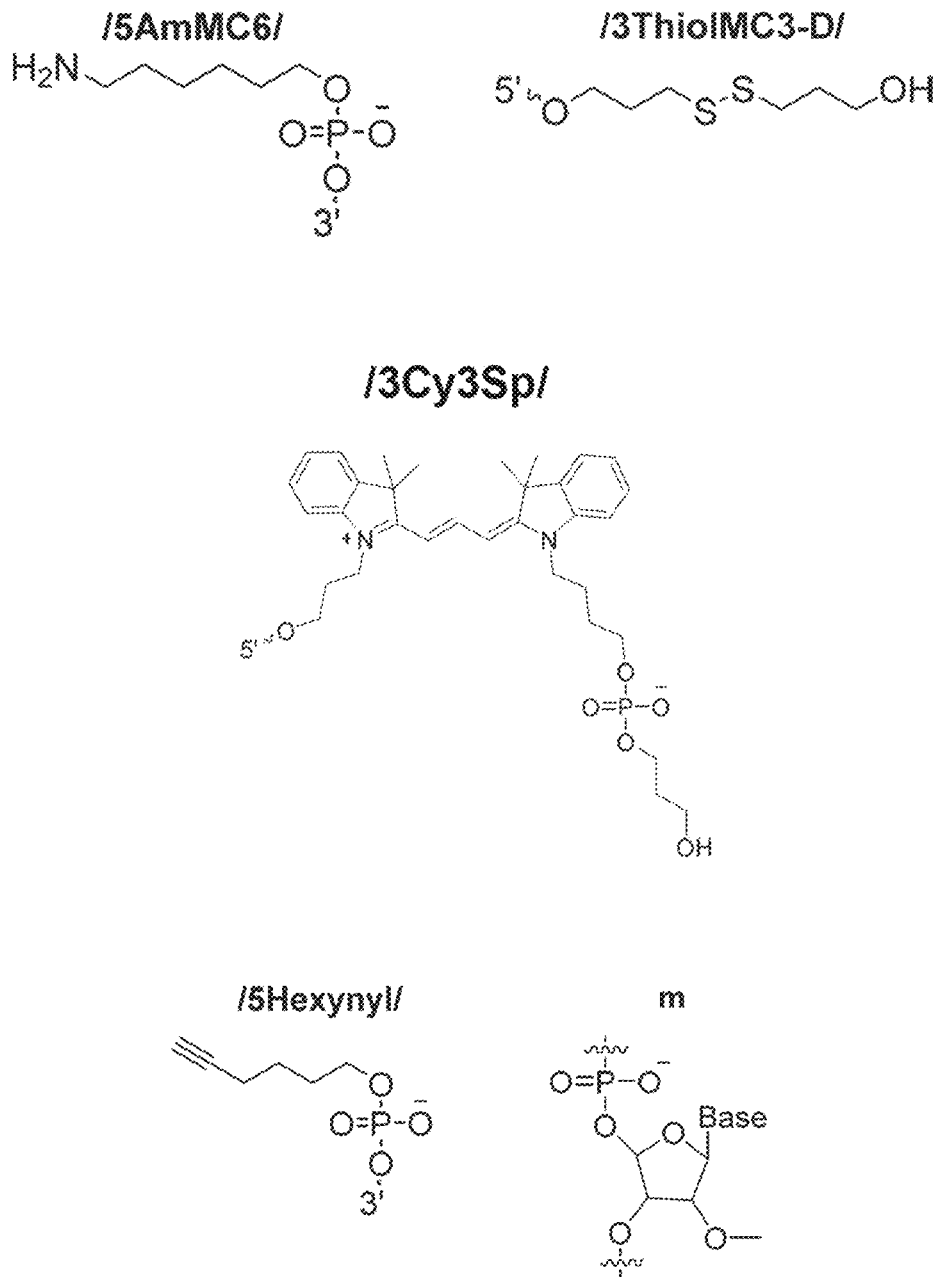
FIG. 1C illustrates the chemical structures of the molecules conjugated to the oligonucleotides.

As illustrated in FIG. 1, a sample of DNA is isolated from a subject and the 5' end of the DNA has been modified with an alkynyl group to allow coupling of the DNA to the surface of a particle comprising azides to form 1,2,3-triazoles. Providing a particle comprising a single stranded DNA. The substrate comprises a gold surface which is bound through a terminal thiol to a DNA that is hybridized to an RNA. Because the RNA is longer sequence than the substrate bound DNA, the substrate provides a portion of single stranded RNA. The single stranded RNA is capable of hybridizing to the single stranded DNA on the surface particle. Therefore, when the particle is places on the surface of the substrate the single stranded DNA and single stranded RNA bind. Further in the presence of RNase H, the RNA is degraded freeing the DNA on the particle for subsequent movement of the particle through new interactions of DNA and RNA on the surface.

In certain embodiments, the disclosure relates to methods for moving a particle, pair of particles, or rod comprising DNA, comprising: providing a device comprising, a particle or rod comprising a coating of single stranded DNA; a substrate comprising a coating of single stranded RNA; and an endoribonuclease such as RNase H, wherein the single stranded DNA hybridizes to the RNA on the substrate and the particle, pair of particles, or rod is configured on the substrate such that the particle, pair of particles, or rod moves upon mixing the endoribonuclease with the DNA hybridized to the RNA; placing the single stranded DNA coated particle on the surface of the single stranded RNA coated substrate in the presence of the endonuclease under conditions such that the particle, pair of particles, or rod moves on the surface of the substrate.

In certain embodiments, DNA or RNA is a sequence obtained from a sample. In certain embodiments, the speed of the movement of the particle is correlated to the sequence of the DNA or RNA. In certain embodiments, a maximum speed is associated with complete complementarity. In certain embodiments, a speed of less than the maximum speed is associated with incomplete complementarity. In certain embodiments, a pair of primers are used to obtain a predetermined DNA sequence from a sample of the subject. The primers may target RNA, e.g., mRNA, or DNA that is in the sample.

In certain embodiments, the disclosure contemplates a kit comprising: a pair or primers, a substrate that contains a DNA bound to the surface, and an oligonucleotide conjugated to a fluorescent marker wherein the oligonucleotide has a first segment that is complementary to the DNA bonded to the surface of the substrate and a second segment that is complementary to a DNA sequence that is to be obtained from a sample by application from the pair of primers. The DNA sequence that is to be obtained from the sample is amplified from a pair of primers. The sequences of the primers may be removed prior to placing the single stranded DNA on the particle through the use of sequence specific restrictions enzymes built into the primers.

Other configurations are contemplated such as the particle, pair of particles, or rod having a capture DNA already attached to the particle. In certain embodiments, the disclosure relates to kits comprising: a particle, pair or particles, or rod comprising a capture DNA; a substrate comprising a coating of single stranded RNA; and a pair of primers configures to amplify a nucleic acid that is complementary to the single stranded RNA and an endoribonuclease. In certain embodiments, the pair of primers is a first primer and a second primer, wherein the first primer is a sequence that has a sequence of five or more nucleotides that are identical or complementary to the single stranded DNA conjugated to the particle, pair of particles, or rod and the second primer has a sequence of five or more nucleotides that are identical or complementary to a sequence of the single stranded RNA.

In certain embodiments, the disclosure relates to kits comprising: a particle, pair or particles, or rod comprising a group reactive the 3' of 5' end of single stranded DNA; a substrate comprising a coating of single stranded RNA; and a pair of primers configures to amplify a nucleic acid that is complementary to the single stranded RNA and an endoribonuclease.

Design and Synthesis of Spherical RNase H Powered Motors

In certain embodiments, an embodiment of this disclosure is a motor which consists of a DNA-coated spherical particle (5 μm or 0.5 μm diameter particles) that hybridizes to a surface modified with complementary RNA. The particle moves upon addition of RNase H, which selectively hydrolyses hybridized RNA but not single stranded RNA. Since the driving force for movement is derived from the free energy of binding new single stranded RNA that biases Brownian motion away from consumed substrate (FIG. 1A), this type of motion is often described as a "burnt-bridge Brownian ratchet". Note that molecular walkers also employ a burnt bridge mechanism, where oligonucleotide hybridization is followed by DNAzyme/endonuclease hydrolysis of the fuel strand. The main difference between the molecular walkers and our system is the massive multivalency of the DNA coated particles—molecular walkers typically employ 2-6 anchor points while our particle-based motor employs thousands of anchoring strands. This equates to 100-1000 fold greater contact area or 10-100 fold greater contact diameter with the surface when compared to molecular spiders. Hence, the micron sized length scale of the particle significantly increases the number of contacts with the surface, which should lead to collective and emergent properties not expected for DNA-based walkers.

Highly multivalent motors display greater processivity, thus addressing a major limitation of DNA walkers. The spherical particle template allows for the potential to roll, which is a fundamentally different mode for translocation of DNA based machines.

An RNA-monolayer was generated on a substrate by immobilizing a DNA anchor strand to a thin gold film and then hybridizing a fluorescently labeled RNA-DNA chimera strand to the surface. A Cy3 fluorophore at the 3' RNA terminus was used to optimize RNA density and to detect RNA hydrolysis using fluorescence microscopy (FIG. 1B). Using the optimized conditions, a maximum RNA density of 50,000 molecules/$\mu m^2$ was achieved, equivalent to an average molecular footprint of 20±6 $nm^2$ per RNA strand. This RNA density was maintained for at least 4 hrs in 1×PBS and 10 μM DTT, a thiol reducing agent necessary for maintaining RNase H activity. In the absence of DTT, surfaces were stable for weeks in 1×PBS.

Given that particle motion is intimately connected with RNase H efficiency and enzyme rates vary when substrates are immobilized, hydrolysis kinetics were measured for a DNA-RNA duplex monolayer. Initially, when measuring the hydrolysis of surface immobilized RNA, RNase H was completely inhibited. Since RNase H contains multiple cysteine residues, it was suspected that enzyme inhibition was due to irreversible binding of the enzyme to the Au surface. To prevent nonspecific binding, the Au surface was passivated with $SH(CH_2)_{11}(OCH_2CH_2)_6OCH_3$ (SH-PEG) in order to reduce nonspecific interactions with surface. To test the assumption that RNase H inhibition was due to Au film binding, the DNA monolayer surface was backfilled with SH-PEG under a range of conditions, where the SH-PEG concentration and the passivation time was varied. It was determined that complete surface passivation occurred after 4 hrs of incubation with a 100 μM SH-PEG solution. This was inferred by observing a saturation in the loss of fluorescence of FAM labeled DNA anchor strand. Next, RNase H hydrolysis of surface immobilized RNA duplexed with DNA was investigated under the various passivation conditions by measuring the loss in fluorescence of Cy3 labeled RNA throughout the channel over time. When the channel was SH-PEG passivated for shorter durations (2 hrs), the fluorescence intensity varied significantly across the length of the well; regions near the port where RNase H was added had the lowest intensities, while regions furthest away from this site showed minimal substrate hydrolysis. In contrast, channels that were blocked for 6 hrs showed homogeneous fluorescence intensities indicating uniform RNase H activity levels.

Figure 2A:
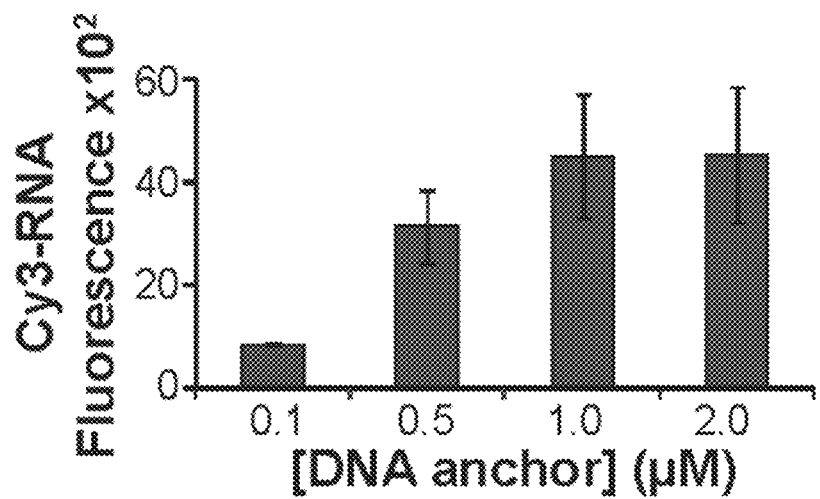
FIG. 2A shows bar graph with data indicating the DNA anchor strand incubation concentration alters the Cy3-RNA fluorescence intensity which is directly proportional to the RNA surface density. The maximum RNA surface density was achieved when the DNA anchor strand incubation concentration was equal to or greater than 1 µM. Error bars represent the standard deviation in the average fluorescence intensity from at least 5 regions across each channel.
Figure 2B:
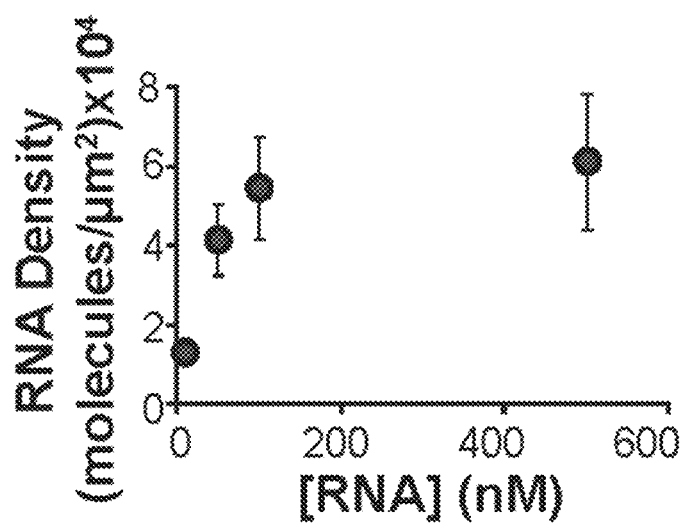
FIG. 2B shows a plot indicating the RNA surface density as a function of RNA concentration during Cy3-RNA hybridization with surface immobilized DNA anchor strand. The RNA density was maximized when RNA was hybridized at a concentration of at least 100 nM.
Figure 2C:
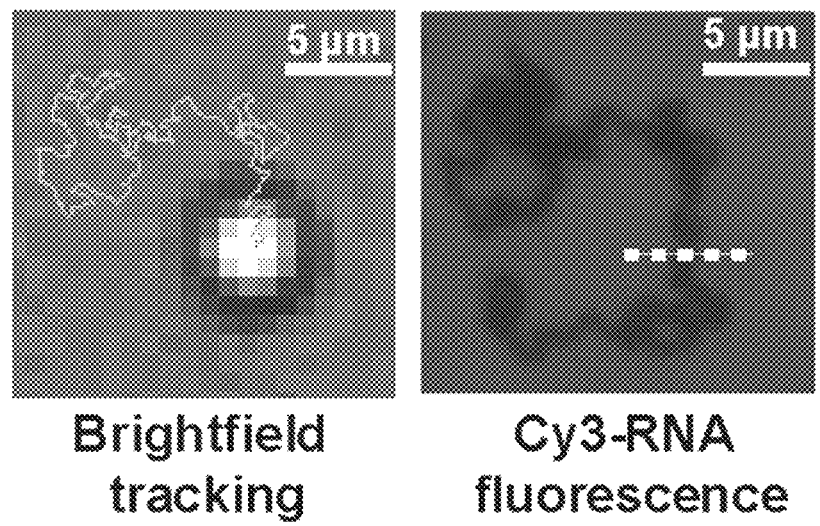
FIG. 2C shows a representative BF image and trajectory (line) from a time-lapse video tracking a single microparticle 30 min following RNase H addition. The same region was then imaged in the Cy3 fluorescence channel, revealing the location of depleted Cy3 signal.
Figure 2D:
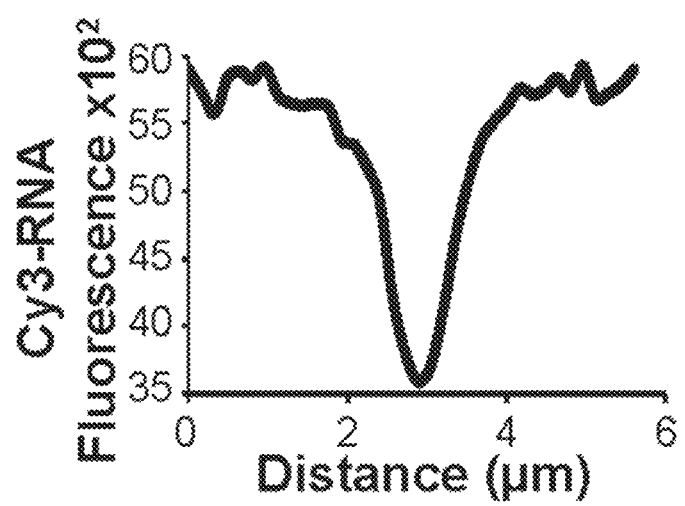
FIG. 2D shows a line scan plot of dashed white line from FIG. 2C showing the depletion track from the widefield fluorescence image.
Figure 2E:
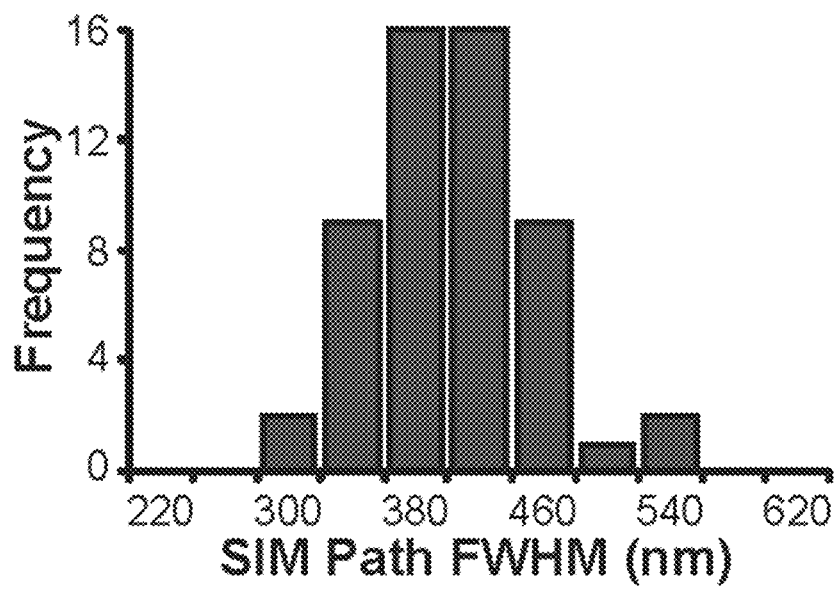
FIG. 2E shows a histogram analysis of FWHM of the depletion path width acquired using structured illumination microscopy.
Figure 2F:
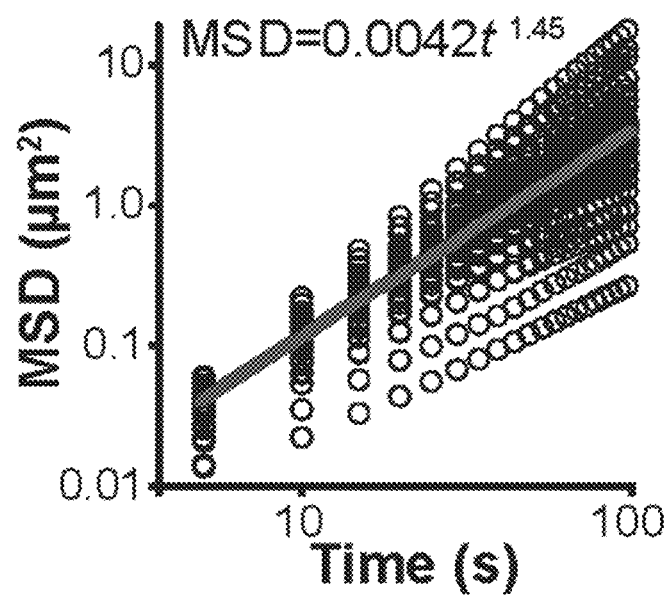
FIG. 2F shows data on the MSD versus log (time) analysis from individual particle trajectories (n=43), which is shown with black circles. The line indicates the average slope derived from all the individual particle trajectories.

DNA-functionalized particles with a density of ~91,000 molecules/μm' (footprint of 11±3 nm2 per molecule) were synthesized and hybridized to a substrate presenting the complementary RNA strand. The DNA density matched that of the RNA density on the planar substrate to ensure a high degree of polyvalency (~104 contacts/$\mu m^2$), therefore minimizing motor detachment from the substrate and maximizing run processivity. Particles remained immobile until RNase H was added, which led to rapid translocation of particles across the substrate. This was quantitatively tracked by finding the centroid of the particles in time-lapse brightfield (BF) microscopy at 5 sec intervals (FIG. 2C). The BF-generated tracks matched the widefield fluorescence depletion tracks (FWHM of 720±110 nm), confirming that the particle motion was associated with continuous RNA hydrolysis (FIGS. 2C and D). The line scan analysis of the fluorescence depletion indicates ~50% of the RNA underneath the particle is hydrolyzed (FIG. 2D). Structured illumination microscopy (SIM), a super resolution microscopy technique with ~110 nm resolution revealed a more accurate footprint of the particle substrate junction corresponding to an average track width of 380±50 nm (n=55 tracks). This footprint indicates a maximum of ~5,500 DNA-RNA surface contacts at the motor-substrate junction (FIG. 2E). Substrates comprised of DNA did not lead to any translocation upon addition of RNase H, confirming that particle motion is specific to RNA hydrolysis at the particle-substrate junction.

Unrestricted Particle Motion

Figure 3A:
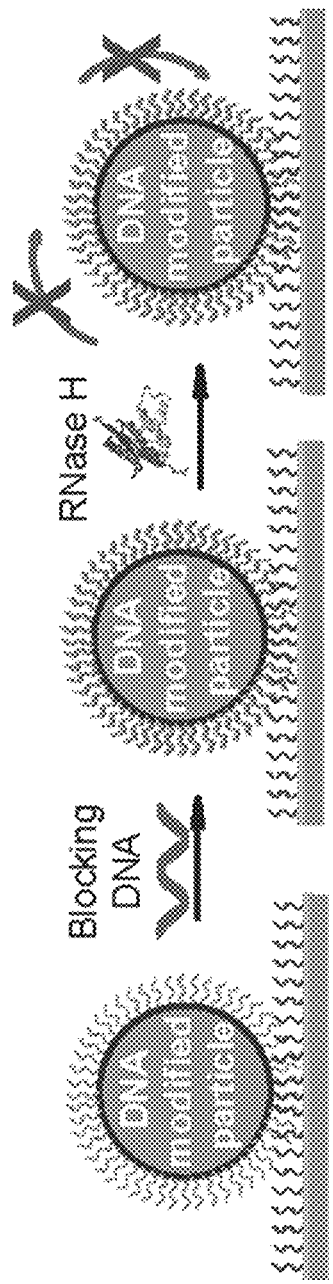
FIG. 3A schematically illustrates the strategy used to test whether particles roll during translocation by blocking the free DNA of the particle by hybridizing with a blocking DNA strand.
Figure 3B:
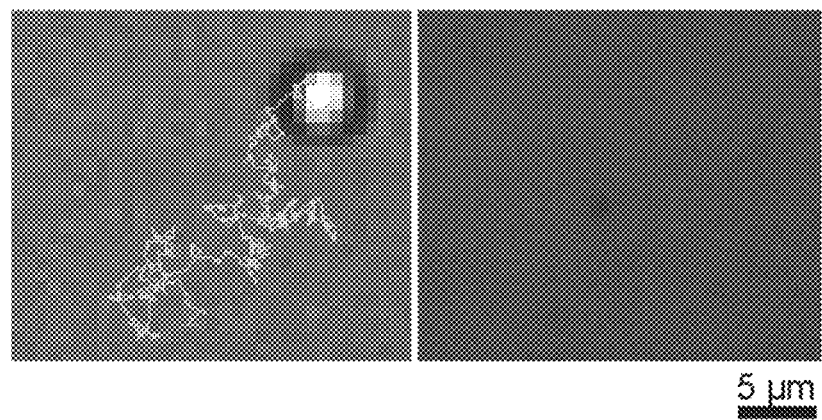
FIG. 3B shows a representative BF image and trajectory taken from a time-lapse video tracking a single particle that had been blocked with DNA and treated with RNase H. The same region was imaged using the Cy3 fluorescence channel, indicating the lack of a RNA hydrolysis track. Note that a small transient spot with lower fluorescence intensity (see center of fluorescence image) is typically observed under particles and is not due to RNA hydrolysis.
Figure 3C:
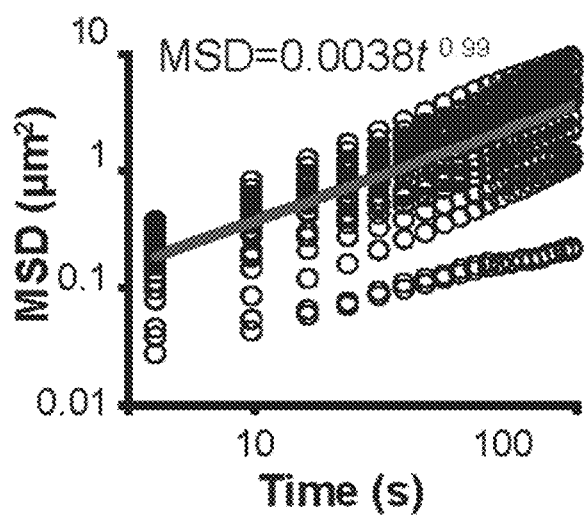
FIG. 3C shows MSD versus log(time) plot of particle diffusion for the blocked particles. The black circles represent individual data points from n=32 particles, while the line indicates the average of these plots.

Particle motion could occur through three plausible mechanisms: a) walking/sliding, b) hopping, and c) rolling. The hopping mechanism was immediately ruled out upon examination of the continuous fluorescence depletion tracks (FIG. 2C). To differentiate between the two remaining mechanisms, particles were hybridized to an RNA substrate, and the unbound DNA on the particle was blocked by hybridization with a complementary DNA strand (FIG. 3A). If motion primarily occurs through a walking/sliding mechanism, particles would move in a processive fashion leaving behind an RNA depletion track. However, upon RNase H addition, particles diffused randomly, producing an $\alpha=0.99\pm0.22$ and a $v=1.8\pm0.8$, and no corresponding RNA depletion tracks were observed (FIGS. 3B and C). By ruling out the hopping and walking/sliding mechanisms of motion, particles primarily translocate by rolling, in a monowheel or cog-and-wheel like fashion. This is the first example of a DNA-based autonomous rolling motor, monowheels.

Figure 3D:
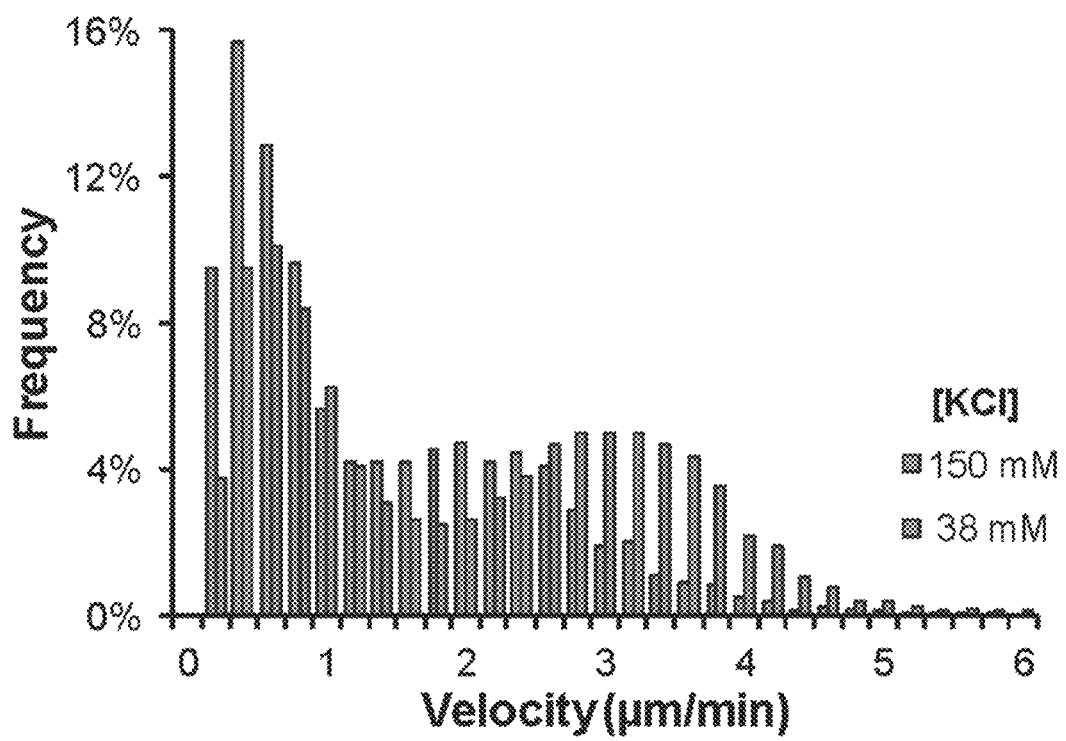
FIG. 3D shows a histogram analysis of particle velocity for each 5 s interval as a function of [KCl]; 38 mM (n=43 particles (15,480 occurrences)) and 150 mM (n=52 particles (18,720 occurrences)).
Figure 3E:
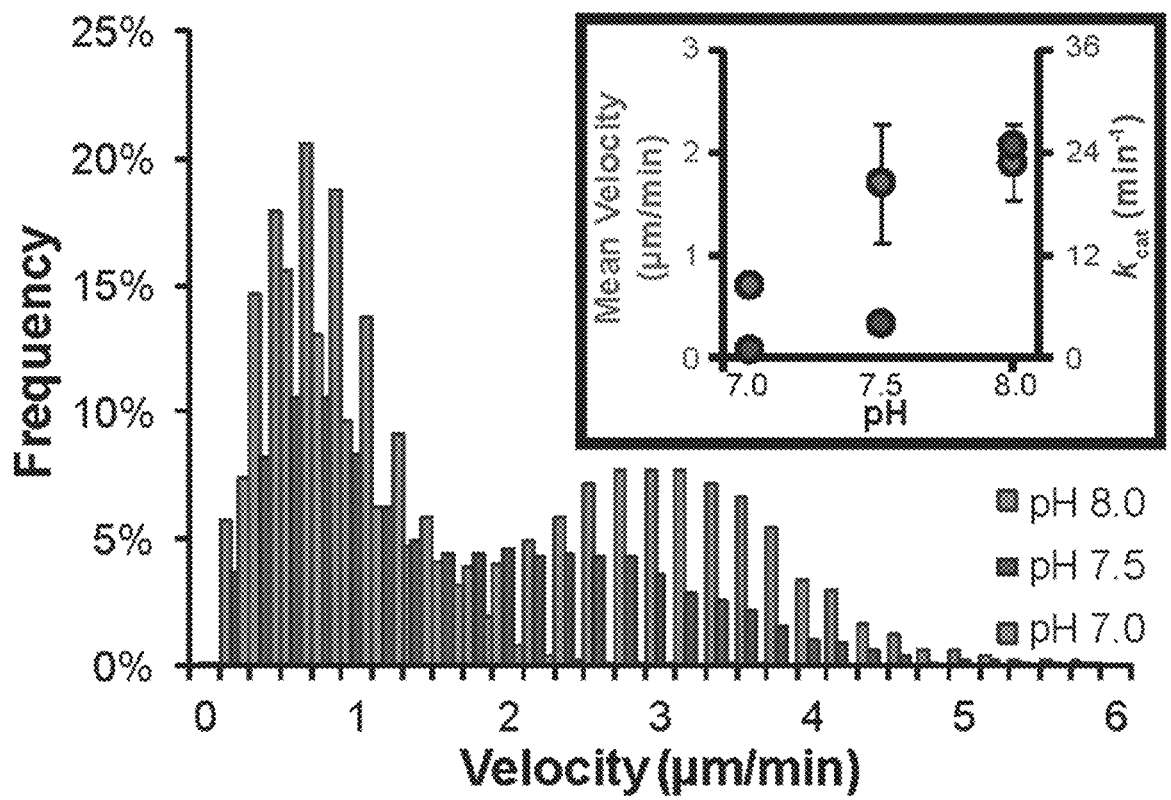
FIG. 3E shows a histogram analysis of particle velocity for each 5 s interval as a function of pH; 8.0 (n=43 particles (15,480 occurrences)), 7.5 (n=50 particles (18,000 occurrences)), and 7.0 (n=26 particles (9,360 occurrences)). Inset compares RNase H kcat and average particle velocity as a function of pH.
Figure 3F:
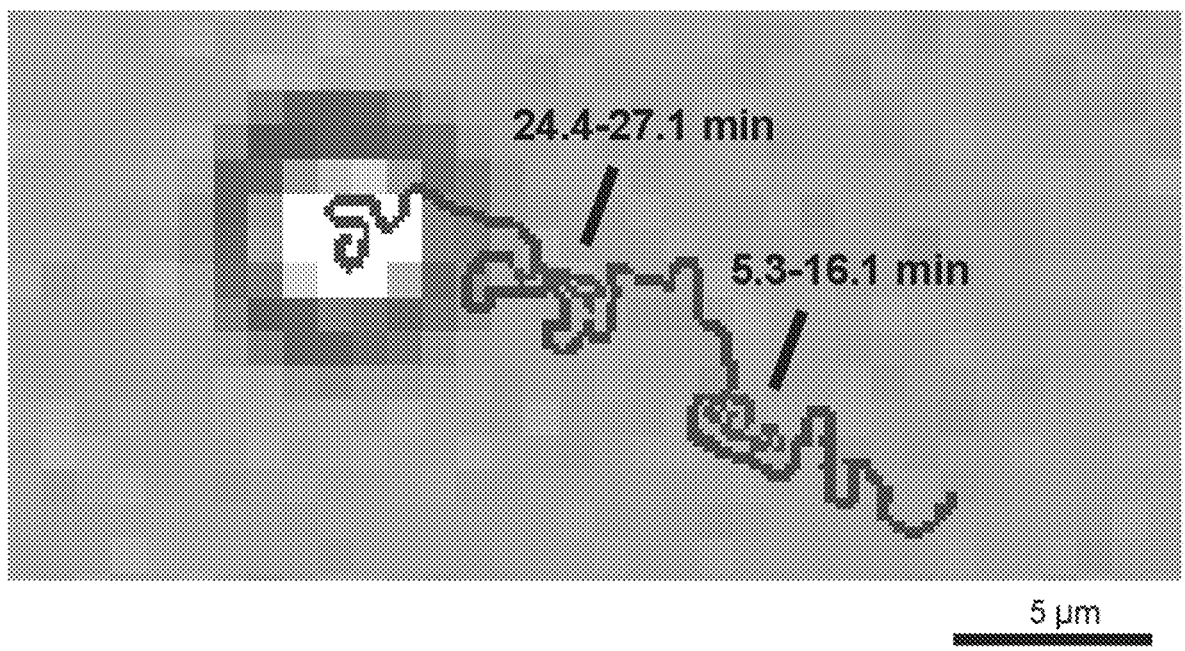
FIG. 3F shows a representative BF image and trajectory taken from a time-lapse video tracking a single particle for 30 min where the section indicates when the particle becomes entrapped.
Figure 3G:
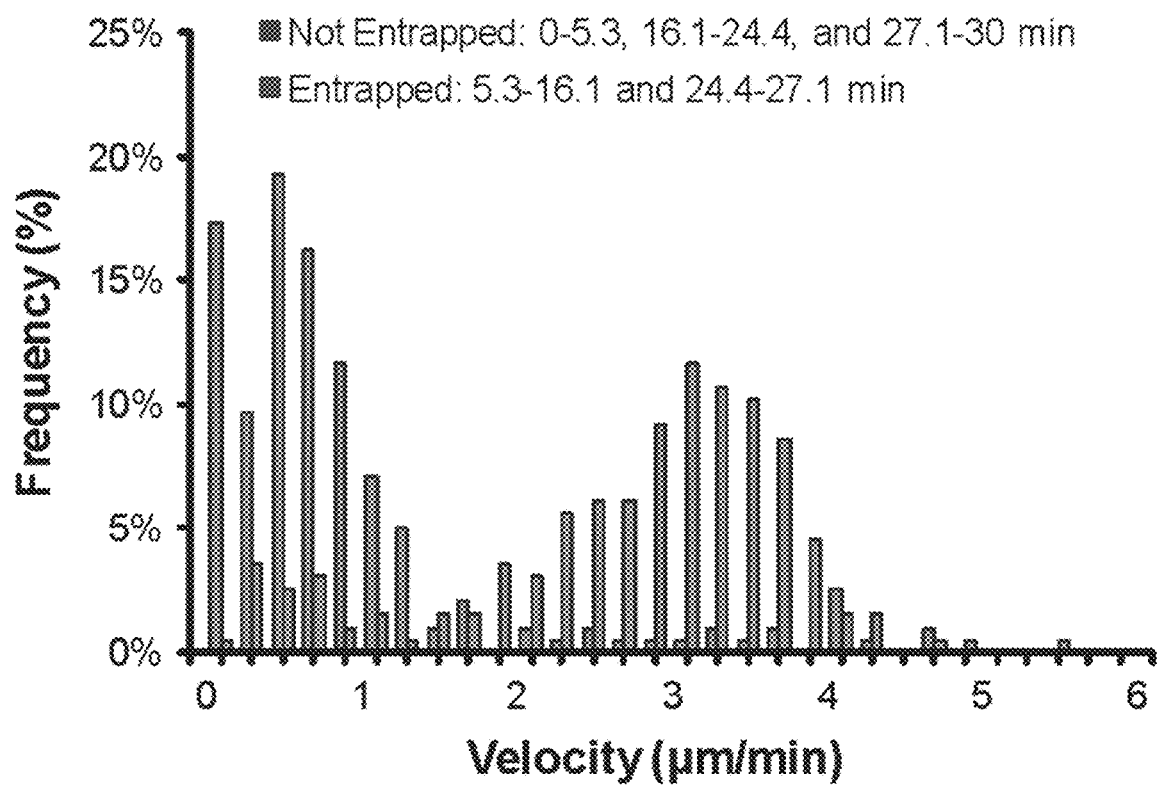
FIG. 3G shows a representative velocity histogram of an individual particle when the particle is entrapped or not entrapped. Entrapment leads to significant decrease in particle velocity.
Figure 3H:
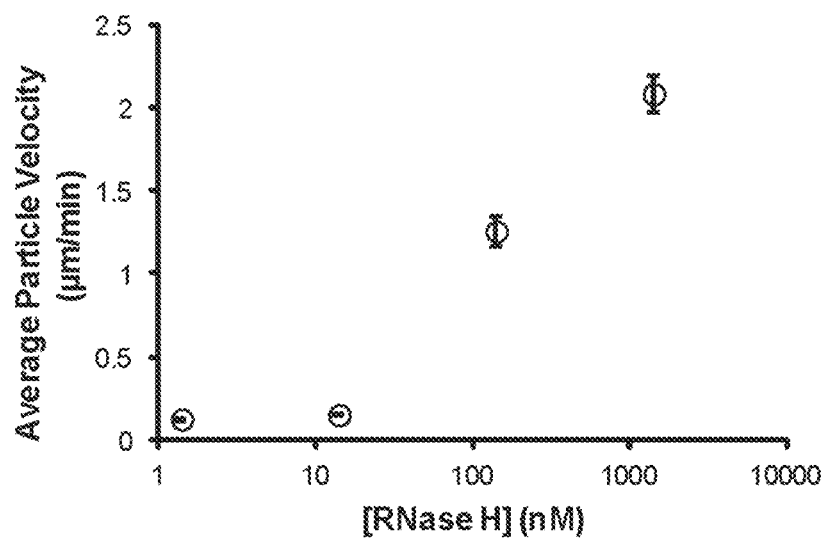
FIG. 3H shows a plot of the particle velocity dependence on RNase H concentration. Note that in the absence of RNase H, the particles do not move.

The particle speed histogram contains two populations (FIG. 3D). Upon further analysis of individual particle velocities and accounting for stage drift, the two populations correspond to two states for each particle, a slow/stalled state and a fast state, as opposed to two types of particles or contributions owing to stage drift. The slower state is due to transient stalling of the particle, which may be attributed to factors that include surface defects leading to non-specific particle binding, inactive enzyme bound to the particle-substrate junction, and particle self-entrapment. Upon detailed analysis of individual particle trajectories, stalling mostly correlated to particle entrapment (FIG. 3F, G). To determine whether the enzyme concentration used, [RNase H]=140 nM, saturated the available substrate binding sites, monowheel velocity was monitored as a function of enzyme concentration (FIG. 3$h$). At 10 fold greater enzyme concentration, only a slight increase in average velocity was observed, whereas 10 fold and 100 fold dilution of RNase H led to near abolition of monowheel motion. The particle speed histograms for decreasing RNase H concentration show a gradual decrease in velocity as opposed to a shift to the low velocity population, thus confirming that multiple RNase H enzymes are operating in parallel.

Particles of 5 μm in diameter were used for the majority of experiments. However, note that the rolling mechanism of translocation can be recapitulated with 0.5 μm diameter particles. Similar maximum velocities up to 5 μm/min and average velocities of 1.8±0.4 and 1.9±0.5 μm/min were observed for both 0.5 and 5 μm particles, respectively, showing that the fundamental cog-and-wheel mechanism of rolling is independent of cargo size within the range tested. The less multivalent 0.5 μm particles roll for shorter average run lengths compared to 5 μm diameter particles (~3 μm versus ~200 μm), which continue processively moving throughout the 30 min video and even continue moving for over 5 hrs. Increasing the KCl and Mg concentrations to 75 mM and 3 mM, respectively, enhances 0.5 μm particle endurance such that the majority of particles display processive motion for the entire 30 min video. This provides the 0.5 μm particles with an average run length of greater than 25 μm.

Unidirectional Motion

Figure 4A:
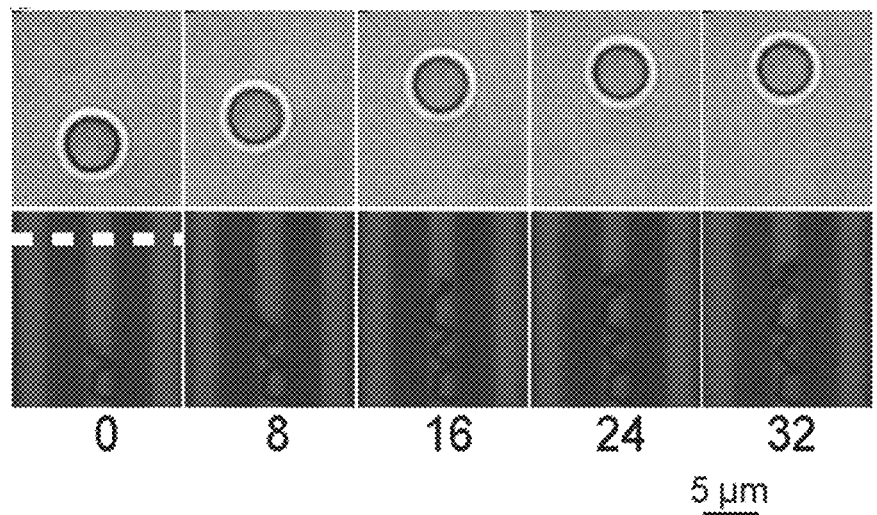
FIG. 4A shows directional motor translocation by time-lapse images of a particle moving along a 3 µm wide track following the addition of RNase H. A strategy was used to generate RNA micro-tracks by using microcontact printing. SH-PEG barriers were directly printed onto the gold film, which was backfilled with RNA.
Figure 4A:
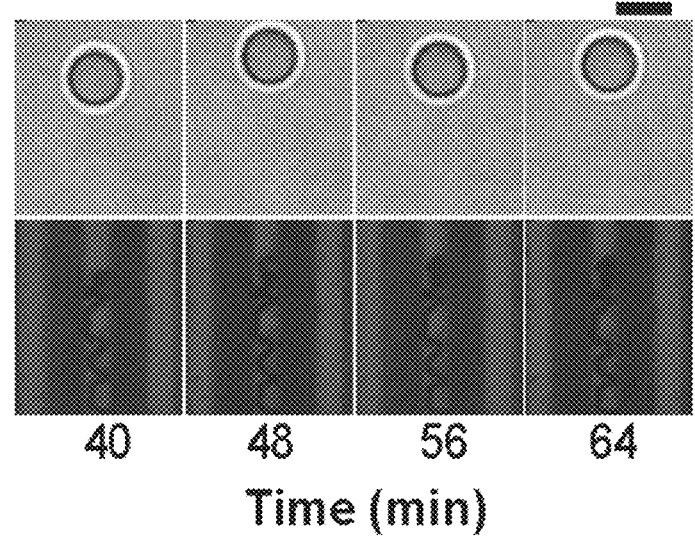
Figure 4B:
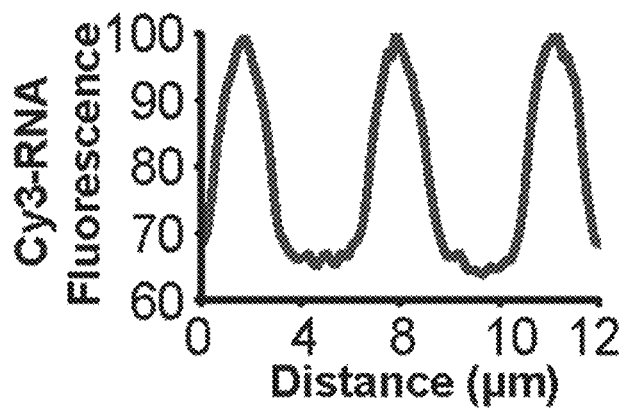
FIG. 4B shows a line scan analysis of the region highlighted in the fluorescence channel with a dotted white line showing the track dimensions and the effectiveness of the PEG barriers.

To achieve unidirectional transport resembling motor protein motion along a filament, RNA was spatially micro-patterned into 3 μm wide tracks. Particles were then hybridized to the patterned RNA, and RNase H was added to initiate motion. Using BF time-lapse tracking and RNA fluorescence depletion, a subset of particles moved along the 3 μm substrate corral unidirectionaly deflecting away from the PEG-printed regions was observed (FIG. 4A). Note that many particles became entrapped, partially because of RNA cross contamination into the PEG-passivated regions (FIG. 4B) and self-entrapment in consumed substrate corrals. It is likely that generating well-passivated nanoscale RNA tracks commensurate in size to the particle-substrate junction width (~400 nm) would lead to an increase yield of linear trajectories.

Figure 4C:
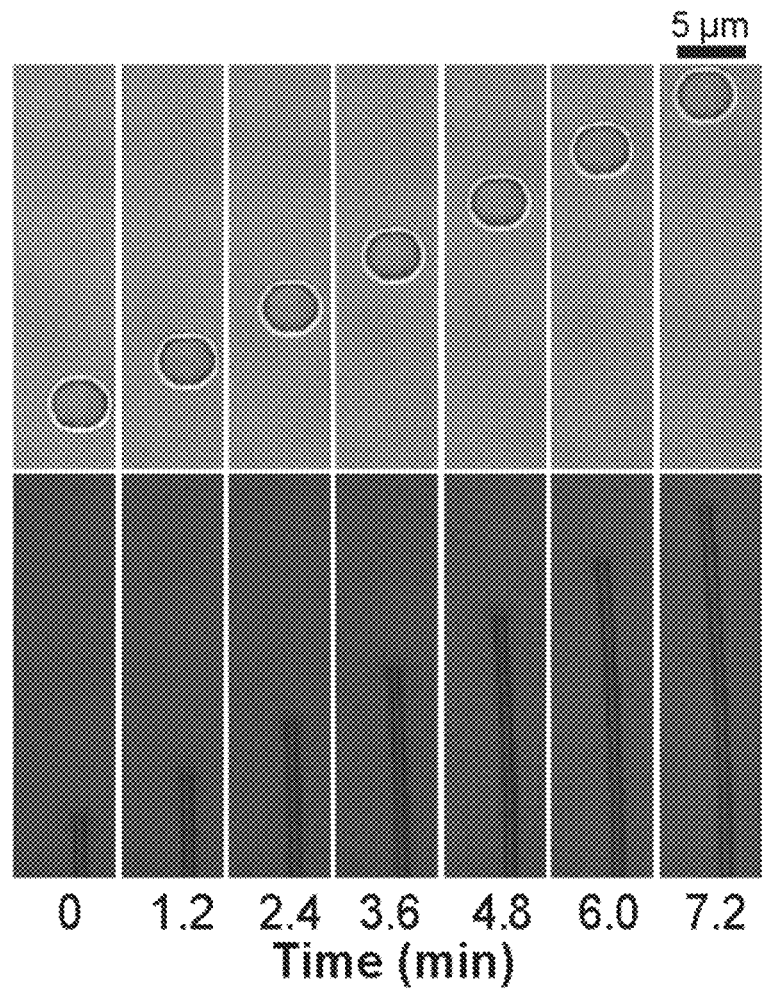
FIG. 4C shows representative BF and fluorescence images taken from a time-lapse movie that tracked a dimerized particle following RNase H addition. The BF-analyzed trajectory as well as the two parallel fluorescence depletion tracks showed near linear particle motion.
Figure 4D:
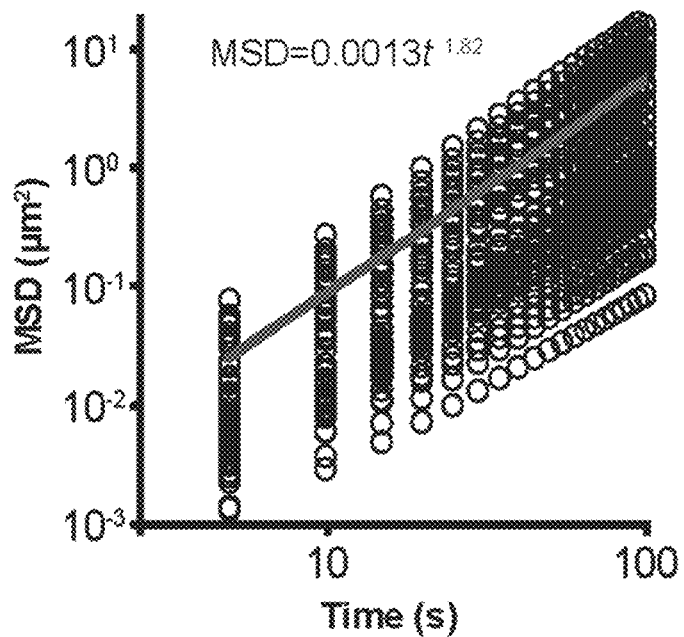
FIG. 4D shows MSD versus log(time) analysis of the dimerized particle motion. Slope of this plot shows an average power log dependence of 1.82±0.13, confirming that the particle dimer traveled in a ballistic, linear fashion.

An alternate strategy to achieve linear motion is to limit lateral particle motion by incorporating multiple monowheels on the body of a single chassis. By happenstance, it was noticed that a 1-10% subset of our particles were fused forming dimers, a common byproduct in silica particle synthesis. These particles traveled linearly for distances that spanned hundreds of μm's at a velocity of ~0.6±0.5 μm/min, n=68 dimer particles (FIG. 4C). A plot of MSD versus t for particle dimers showed a power-law scaling of $\alpha=1.82\pm0.13$, confirming that particle motion was nearly linear ($\alpha=2$). In addition, 50% of single spherical particles displayed a transient component of their trajectory that is linear and associated with wider tracks; linear motion was correlated with wider ~1.0±0.1 μm tracks or multiple contact points. The ballistic (linear) motion observed for what appears to be wider tracks may be due to particles possessing multiple contact points that cannot be resolved or due to particles rolling along imperfections along the surface. Following these observations, DNA-coated microrods were synthesized. Microrods showed nearly linear motion. These are the first examples of directional motion without the need of a patterned track or external electromagnetic field, which is only afforded due to the unique cog-and-wheel translocation mechanism.

SNP Detection by Measuring Particle Displacement

Figure 5:
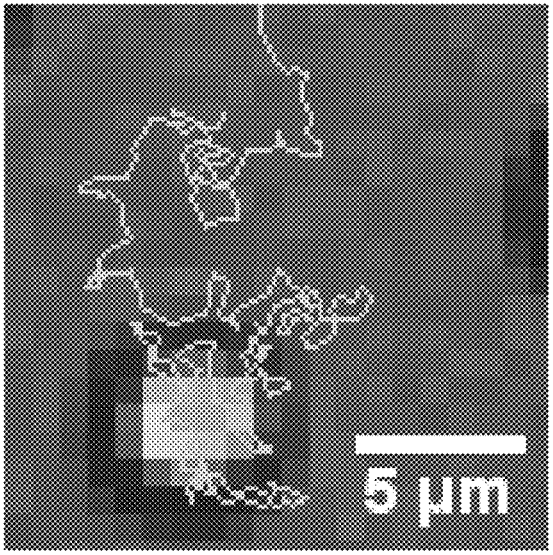
FIG. 5 illustrates an example of single nucleotide polymorphism (SNP) detection using bright field images. The images show particles and their net displacement for perfect match and SNP sequences after RNase H addition. The sequences are illustrated below each.
Figure 5:
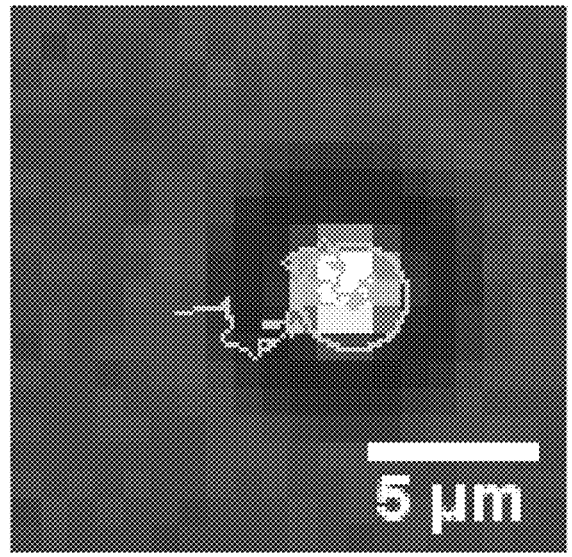

Since monowheel motion is sensitive to $k_{on}$, $k_{off}$ and $k_{cat}$, particle motion could provide a readout of molecular recognition. Particles displaying the SNP (5'mAmGTAATTAA-mUmC3') traveled ~60% slower (0.3 μm/min) than identical particles with a perfect match (5'mAmGTAATCAA-mUmC3'). This difference in velocity can be attributed to a slower rate of hydrolysis for RNase H to hydrolyze duplexes possessing a single base mismatch. Due to the μm-sized cargo and large distances traveled, even a smartphone camera equipped with an inexpensive plastic lens could detect motion associated with this SNP by recording particle displacement within a short time interval (t=15 min). SNP detection could also be achieved using unmodified DNA (FIG. 5); although maximum discrimination required shortening the RNase H recognition sequence.

The invention claimed is:

1. A method for moving a particle comprising DNA, comprising:
providing a rolling particle system comprising,
a spherical particle comprising a coating of single stranded DNA;
a planar substrate comprising a coating of single stranded RNA, wherein the RNA density is between about $2\times10^4$ molecules molecules/µm$^2$ and about $6\times10^4$ molecules/µm$^2$, wherein the RNA is conjugated to a fluorescent molecule, wherein the substrate further comprises polyethylene glycol; and
RNase H; and
placing the single stranded DNA coated particle on the surface of the planar substrate in the presence of RNase H such that the particle moves on the surface of the substrate.

2. The method of claim 1, further comprising obtaining a DNA or RNA sequence from a sample of a subject and coating the single stranded DNA on the spherical particle with the same DNA or RNA sequence from the sample.

3. The method of claim 2, wherein the DNA or RNA encodes a mutation associated with a genetic disorder.

4. The method of claim 3, wherein the mutation associated with a genetic disorder is a single nucleotide polymorphism.

5. The method of claim 2 further comprising measuring a speed of the movement of the particle.

6. The method of claim 5 further comprising correlating the speed of the movement of the particle to the sequence of the DNA or RNA sequence from the sample, wherein a maximum speed is associated with complete complementarity of the single stranded DNA on the spherical particle to the single stranded RNA on the planar substrate and a speed of less than the maximum speed is associated with incomplete complementarity.

7. The method of claim 1, wherein the DNA is between 5 and 500 nucleotides in length.

8. The method of claim 1, wherein the particle has a diameter of 0.001 micrometers to 1 centimeter.

9. The method of claim 1, wherein the DNA has a density coverage of 91,000 molecules/µm2.

10. The method of claim 1, wherein RNase H is at a concentration of 140 nM or a 10 fold increase thereof.

11. A method for moving a rod comprising DNA, comprising:
providing a rolling particle system comprising,
a rod of two or more spherical particles comprising a coating of single stranded DNA;
a planar substrate comprising a coating of single stranded RNA, wherein the RNA density is between about $2\times10^4$ molecules molecules/µm$^2$ and about $6\times10^4$ molecules/µm$^2$, wherein the RNA is conjugated to a fluorescent molecule, wherein the substrate further comprises polyethylene glycol; and
RNase H;
placing the single stranded DNA coated particle on the surface of the planar substrate in the presence of RNase H such that the rod moves on the surface of the substrate.

12. The method of claim 11, further comprising obtaining a DNA or RNA sequence from a sample of a subject and coating the single stranded DNA on the rod with the same DNA or RNA sequence from the sample.

13. The method of claim 12, wherein the DNA or RNA encodes a mutation associated with a genetic disorder.

14. The method of claim 13, wherein the mutation associated with a genetic disorder is a single nucleotide polymorphism.

15. The method of claim 12 further comprising measuring a speed of the movement of the rod.

16. The method of claim 15 further comprising correlating the speed of the movement of the rod to the sequence of the DNA or RNA sequence from the sample, wherein a maximum speed is associated with complete complementarity of the single stranded DNA on the rod to the single stranded RNA on the planar substrate and a speed of less than the maximum speed is associated with incomplete complementarity.

17. The method of claim 11, wherein the DNA is between 5 and 500 nucleotides in length.

18. The method of claim 11, wherein the DNA has a density coverage of 91,000 molecules/µm2.

19. The method of claim 11, wherein RNase H is at a concentration of 140 nM or a 10 fold increase thereof.

* * * * *